United States Patent
Brik et al.

(10) Patent No.: US 9,079,966 B2
(45) Date of Patent: Jul. 14, 2015

(54) CHEMICAL PREPARATION OF POLYUBIQUITIN CHAINS

(75) Inventors: Ashraf Brik, Be'er Sheva (IL); Mahmood Haj-Yahya, Taybe-Meshulash (IL); Ajish Kumar, Kochi (IN); Leslie Erlich, Hertzliya (IL); Liat Spasser, Hertzliya (IL)

(73) Assignee: BEN-GURION UNIVERSITY OF THE NEGEV RESEARCH AND DEVELOPMENT AUTHORITY, Beer-Sheva (IL)

( * ) Notice: Subject to any disclaimer, the term of this patent is extended or adjusted under 35 U.S.C. 154(b) by 72 days.

(21) Appl. No.: 13/578,015

(22) PCT Filed: Feb. 9, 2011

(86) PCT No.: PCT/IL2011/000137
§ 371 (c)(1), (2), (4) Date: Oct. 15, 2012

(87) PCT Pub. No.: WO2011/098998
PCT Pub. Date: Aug. 18, 2011

(65) Prior Publication Data
US 2013/0060003 A1    Mar. 7, 2013

Related U.S. Application Data

(60) Provisional application No. 61/302,559, filed on Feb. 9, 2010.

(51) Int. Cl.
| | |
|---|---|
| C07K 1/00 | (2006.01) |
| C07K 1/107 | (2006.01) |
| C07K 14/00 | (2006.01) |
| C07K 14/435 | (2006.01) |
| C07K 14/47 | (2006.01) |

(52) U.S. Cl.
CPC .................. *C07K 14/47* (2013.01); *C07K 14/00* (2013.01)

(58) Field of Classification Search
CPC ...... C07K 14/47; C07K 14/001; C07K 14/01; C07L 1/006; C07L 1/00; A61K 38/17; A61K 38/16; A61K 38/00
See application file for complete search history.

(56) References Cited

U.S. PATENT DOCUMENTS

| | | |
|---|---|---|
| 4,775,676 A | 10/1988 | Chiesi et al. |
| 2009/0220470 A1 | 9/2009 | Rodriguez et al. |

OTHER PUBLICATIONS

Pickart et al., Methods in Enzymology (2005) 399, 21-36.*
Piotrowski et al., J. Biol. Chem. (1997) 272, 23712-23721.*
Love et al., Biochem J. (1997) 323, 727-734.*
Pickart Cecile M et al: "Controlled synthesis of polyubiquitin chains", Methods in Enzymology; [Methods in Enzymology], Academic Press, US, val. 399, Jan. 1, 2005, pp. 21-36, XP009171092.
Kumar et al: "Highly Efficient and Chemoselective Peptide Ubiquitylation", Angewandte Chemie International Edition, vol. 48, No. 43, Oct. 12, 2009, pp. 8090-8094, XP055066201.
Jung J et al: "Synthesis and high resolution mass spectrometric structural characterization of polyubiquitin conjugates", Journal of Peptide Science, vol. 12, No. Suppl. S, 2006, p. 128, & 29th European Peptide Symposium; Gdansk, Poland; September 3-8, 2006.
Jieun Jung et al: "Functional Ubiquitin Conjugates with Lysine-.epsilon.-Amino-Specific Linkage by Thioether Ligation of Cysteinyi-Ubiquitin Peptide Building Blocks", Bioconjugate Chemistry, ACS, Washington, DC, US, vol. 20, No. 6, Jun. 17, 2009, pp. 1152-1162.
Renliang Yang et al: "Dual Native Chemical Ligation at Lysine", Journal of the American Chemical Society, vol. 131, No. 38, Sep. 30, 2009, pp. 13592-13593, XP055070521.
Mahmood Haj-Yahya et al: "Protecting group variations of [delta]mercaptolysine useful in chemical ubiquitylation", Biopol Ymers, vol. 94, No. 4, Jun. 3, 2010, pp. 504-510, XP055066339.
Farid El&EMSP14;Oualid et al: "Chemical Synthesis of Ubiquitin, Ubiquitin-Based Probes, and Diubiquitin", Angewandte Chemie International Edition, vol. 49, No. 52, Dec. 27, 2010, pp. 10149-10153, XP055016044.
Renliang Yang et al: "Synthesis of K48-linked diubiquitin using dual native chemical ligation at lysine", Chemical Communications, vol. 46, No. 38, Aug. 25, 2010, p. 7199, XP055070531.
Langdon J. Martin et al: "Carpe Diubiquitin", Angewandte Chemie International Edition, vol. 49, No. 48, Nov. 22, 2010, pp. 9042-9044, XP055070526.
K. S. Ajish Kumar et al: "Total Chemical Synthesis of Di-ubiquitin Chains", Angewandte Chemie International Edition, vol. 49, No. 48, Nov. 22, 2010, pp. 9126-9131, XP055066534.
K. S. Ajish Kumar et al: "[delta]-Mercaptolysine Assisted Ubiquitination", Israel Journal of Chemistry, vol. 51, No. 8-9, Aug. 30, 2011, pp. 900-907, XP055070529.
Pasunooti et al. Synthesis of 4-mercapto-1-lysine derivatives: Potential building blocks for sequential native chemical ligation. Bioorganic & Medicinal Chemistry Letters 2009, 19(22):6268-6271; p. 6268, col. 1.
Hejjaoui, Henaoui et al. Towards Elucidation of the Role of Ubiquitination in the Pathogenesis of Parkinson's Disease with Semisynthetic Ubiquitinated a-Synuclein. Angew. Chem. Int. Ed. Jan. 2011, 50(2):405-409.
Bang et al. Kinetically Controlled Ligation for the Convergent Chemical Synthesis of Proteins. Angew. Chem. Int. Ed. 2006, 45:3985-3988.
Supplementary European Search Report issued in corresponding European Patent Application No. EP11741975 dated Jul. 29, 2013.

* cited by examiner

*Primary Examiner* — Karlheinz R Skowronek
*Assistant Examiner* — Catherine Mader
(74) *Attorney, Agent, or Firm* — Browdy and Neimark, PLLC

(57) ABSTRACT

The present invention discloses a process for the preparation of a Poly-ubiquitin chain, this process comprising ligating a Ubiquitin thioester Ubm-SR with a Ubiquitin Ubq. Further are disclosed poly-ubiquitin chains prepared according to this process, in particular poly-ubiquitin chains containing at least one unnatural amino acid.

13 Claims, 4 Drawing Sheets

CHEMICAL PREPARATION OF POLYUBIQUITIN CHAINS

Figure 1:
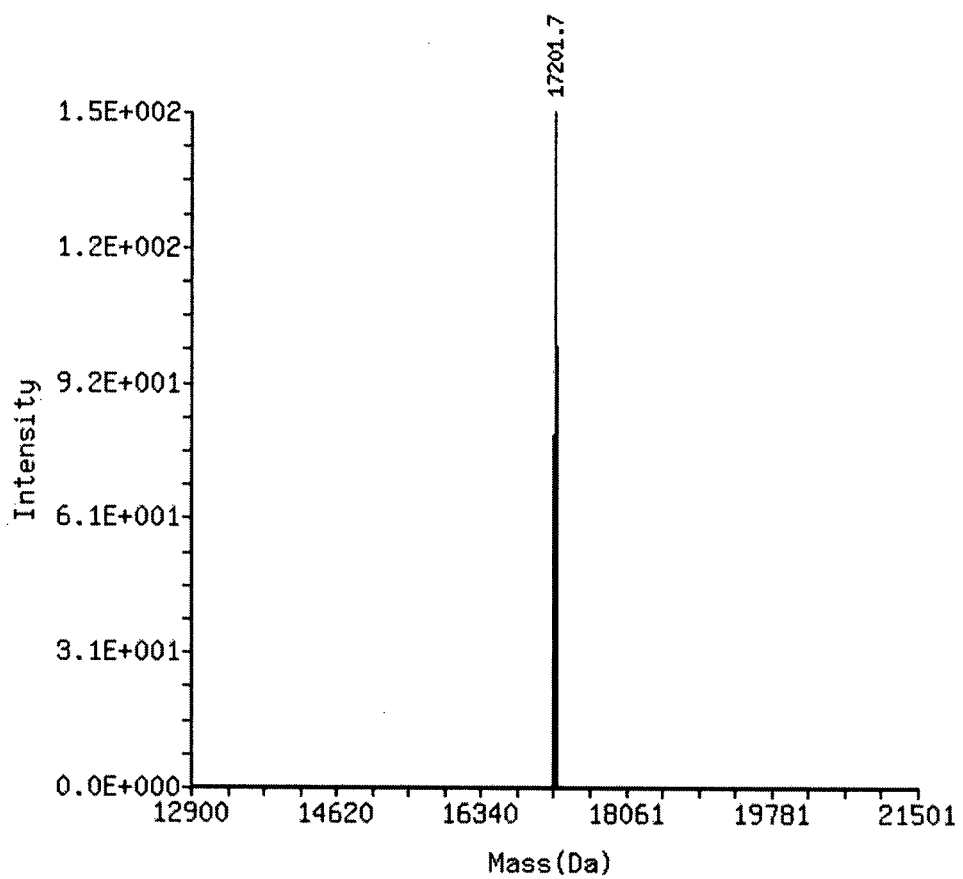

Ubiquitination, the attachment of ubiquitin (Ub) or polyubiquitin (polyUb) chain to a protein target, is involved in a wide range of cellular processes in eukaryotes. The conjugation of Ub molecule can be as a monomer (mono-ubiquitination) or as a chain of various length and linkage types (polyubiquitination). The overall process of ubiquitin-dependent metabolism is a multi-enzymatic process requiring the successive activities of distinct conjugating (E1s, E2s, E3s) and deubiquitinating enzymes (DUBS). The type and number of poly-ubiquitin chains (polyubiquitination vs monoubiquitination) that are conjugated to a target is highly regulated to generate distinct signals that affect different physiological processes (e.g. regulation of endocytosis and DNA repair).

Polyubiquitination is a complex and diverse modification where the outcome of molecular signal depends on which one of the seven lysines in Ub (K6, K11, K27, K29, K33, K48, K63) is linked to consecutive Ub molecules. The connectivity of the chain through K48 of Ub is called a typical chain, while through any one of the other six lysines are known as atypical chains. The latter can be homotypic in which a single type of lysine is used for the chain assembly, mixed-linkage with several distinct lysines involved in the branching of Ub chain, or heterologues wherein Ub and Ub-like modifiers e.g. SUMO, are utilized in the assembly of the chain.

Multi-ubiquitin chains are built by formation of an isopeptide bond between Gly76 of one ubiquitin to the $\epsilon$-NH$_2$ group of one of the seven potential lysines of the preceding ubiquitin. While all lysines can participate in Ub chain formation, five (K6, K11, K29, K48 and K63) are known to be major sites of initiation and these linkages exist in vivo as anchored and unanchored species.

Presently, ubiquitin chains are commercially synthesized using the E1-E3 enzymatic machinery in which the identification of the enzymatic systems is considered to be the main challenge, and is currently mainly limited to K-48 and K-63 linkages.

However, the appreciation of the functional and structural diversity of Ub chain signals and the fact that little is known about the various aspects of the atypical Ub chains has generated an urgent need for milligram quantities of homogeneous Ub chains with a high purity of well-defined chain length and linkage type to assist structural, biochemical and biophysical studies.

Unfortunately, the unusual connectivity in Ub chain i.e. the isopeptide bond and their relatively big size presents a real challenge to an organic chemist where unprecedented chemistry must be developed to achieve the total chemical synthesis of such a natural product family.

Recently, a new method for highly efficient and chemoselective peptide (substrate) ubiquitylation has been reported by some of the present inventors (Kumar et al. *Angew. Chem. Int. Ed.* 2009, 48, 8090-8094), utilizing a δ-mercaptolysine residue.

It has now been found by the present inventors that poly-ubiquitin chains can be formed by a transthioesterification reaction of a 1,2-thioamine-containing first ubiquitin with a second Ub thioester, followed by S—N acyl transfer. Subsequently, the thiol "handle" can be removed by applying the desulfurization reaction to furnish the unmodified isopeptide linkage between the Ub thioester and the Ub.

In order to obtain a poly-ubiquitin containing more than 2 Ub monomers, either sequential ligation or convergent ligation must take place.

The sequential ligation is based on the sequential addition of a Ub thioester monomer, to the growing poly-ubiquitin chain which started from the 1,2-thioamine-containing first ubiquitin Ub as described hereinabove. In this case it is essential that the Ub thioester monomer is designed to contain a protected 1,2-thioamine-containing amino acid in each addition step, whereas following the ligation between the thioester and the 1,2-thioamine-containing amino acid in the growing poly-ubiquitin, the protected 1,2-thioamine-containing amino acid that is now present on the newly-obtained poly-ubiquitin chain, is activated by un-masking of the protection group, enabling it to participate in yet another addition step with another Ub thioester monomer.

Thus, the process described herein can be repeated for adding additional Ub thioester monomers having 1,2-thioamine "handle" incorporated therein, thus forming Ub polymers/chains of pre-determined sizes. Obviously, the presence of the protected 1,2-thioamine-containing amino acid in the Ub thioester monomer is no longer necessary during the addition of the last Ub thioester monomer.

In the case of convergent ligation, the same general process described above is conducted, whereas either one or both of the Ub thioester and the Ub contain more than one Ub monomers.

Furthermore, since the 1,2-thioamine group can be incorporated at any of the 7 potential locations on the Ub molecule, this new method enables the preparation of a variety of chains having different topologies, thus broadening the scope of possible chains much beyond the limited known biological/enzymatic reactions, and doing this at much lower costs.

Examples of polyubiquitin chains prepared by this process include all di-Ub chains (K6, K11, K27, K29, K33, K48, K63), trimers (K48) and tetramers (K48), but the process can be applied practically with no limitations to prepare a poly-ubiquitin of any desired length and combination of linkages, by ligating a Ubiquitin (Ub) thioester Ub$_m$-SR with a Ubiquitin Ubq, thereby obtaining a poly-ubiquitin chain Ub$_n$, comprising n ubiquitin monomers linked by isopeptide bonds, n being an integer larger than 1.

Thus, according to a first aspect of the invention, there is now provided a process for the preparation of a Poly-ubiquitin chain Ub$_n$, comprising n ubiquitin monomers linked by isopeptide bonds, n being an integer larger than 1, this process comprising:

a) ligating a first Ubiquitin (Ub) thioester unit Ub$_m$-SR with a second ubiquitin unit Ubq, wherein the Ub thioester unit Ub$_m$-SR contains m ubiquitin monomers, m being an integer ranging from 1 to (n−1), further wherein at least one of these monomers contains p protected 1,2-thioamine-containing amino acids, p being an integer ranging from 0 to 7, R being selected from alkyl and aryl, including substituted or unsubstituted derivatives thereof; further wherein the ubiquitin unit Ub$_q$ contains q ubiquitin monomers, q being an integer ranging from 1 to (n−1), further wherein the Ubq unit contains at least one non-protected 1,2-thioamine-containing amino acid, with the proviso that p is at least 1 if (m+q)≠n, and further with the proviso that (m+q) is smaller or equal to n;

to obtain a ligation product Ub$_{m+q}$ having (m+q) ubiquitin monomers and containing the p protected 1,2-thioamine-containing amino acids;

b) when p≠0 and (m+q) is smaller than n, de-masking at least one of the protected 1,2-thioamine-containing amino acids in the ligation product Ub$_{m+q}$ obtained in (a);

c) if (m+q) is smaller than n, repeating (a) and (b), x times, to obtain a final ligation product $Ub_n$ having n Ub monomers in (x+1) steps, whereas in each step, Ubq is the ligation product $Ub_{m+q}$ obtained in the previous step, and Ubm-SR is the same or different as the one used in the previous step;

d) Desulfurization of the ligation product Ubn to obtain the Poly-ubiquitin chain Ubn having n ubiquitin monomers linked by isopeptide bonds.

As used herein, the term "ubiquitin" or Ub includes within its scope all known as well as unidentified eukaryotic Ub homologs of vertebrate or invertebrate origin. Examples of Ub polypeptides as referred to herein include the human Ub polypeptide that is encoded by the human Ub encoding nucleic acid sequence (GenBank Accession Numbers: U49869, X04803) as well as all equivalents.

For example, natural human Ub protein has the following sequence, containing the following 76 amino acids:

MQIFVKTLTGKTITLEVEPSDTIENVKAKIQDKEGIPPDQQRLIFAGKQL EDGRTLSDYNIQKESTLHLVLRLRGG.

Therefore, according to one preferred embodiment, the ubiquitin polypeptide is a natural ubiquitin polypeptide.

However, as used herein, the term "ubiquitin" (Ub) also includes modified ubiquitin polypeptides.

The term "modified Ub" as used herein refers to polypeptides containing the natural Ub sequence, whereas one or more of the 76 amino acids comprising this sequence is modified by a unnatural amino acid.

The term "unnatural amino acid" refers to any amino acid, modified amino acid, and/or amino acid analogue, that is not one of the 20 common naturally occurring amino acids or the rare naturally occurring amino acids e.g., selenocysteine or pyrrolysine.

The term "Ub polypeptide" as used herein refers to a sequential chain of amino acids linked together via peptide bonds to form a Ub unit. The terms "polypeptide" and "protein" may be used interchangeably.

The term "Ub fragment" is used interchangeably with the term "Ub segment" and refers to a sequence of amino acids forming part of the Ub monomer.

For example, in the ensuing examples, an equivalent sequence to natural Ub was synthetically prepared, replacing the Met amino acid with a Leucine amino acid (namely to obtain the following sequence: LQIFVKTLTGKTITLEVE-PSDTIENVKAKIQDKEGIPPDQQRLIF-AGKQLEDGRTLSDYNIQKESTLHLVLRLRGG), thereby avoiding oxidation of the Met. Similarly, another equivalent is obtained by replacing the Met with nurleucine (Nle). However, the invention also works with the original Met amino acid.

Additional examples to modified Ub include replacing Leu amino acids in positions 28 or 46 by a 1,2 thioamine containing amino acid, such as mercaptolysine derivatives, or by introducing a labeled amino acid, or an amino acid linked to a specific reagent etc.

The term "ubiquitin unit" as used herein includes both mono-ubiquitin or a poly-ubiquitin. In other words, the ubiquitin unit can contain one or more ubiquitin monomers.

The term "Ub monomer", used herein interchangeably with the term "mono-ubiquitin", refers to a 76-amino acid sequence of ubiquitin, either natural or modified.

The term "Ub chain" used herein interchangeably with the term poly-ubiquitin, refers to a Ub unit containing more than one Ub monomer.

Furthermore, the term "Ub" also includes Ubiquitin-like-modifiers (ULM), also termed "ubiquitin-like" or "Ubl" protein modifiers. This term, as used herein, refers to the group of small proteins that are subject to conjugation machinery similar to that for ubiquitination. Examples of Ubl protein modifiers include NEDD8, ISG15, SUMO1, SUMO2, SUMO3, APG12, APG8, URM1, Atg8, URM1, HUB1, FUB1, FAT10, UBL5, UFM1, MLP3A-LC3, ATG12, as well as other Ubl protein modifiers yet to be identified.

Ub monomers or "building blocks" (termed hereinbelow Ub1, Ub2, Ub3 and Ub4) are preferably prepared from two peptide fragments (also termed segments) obtained from separate SPPS reactions: an N-terminal fragment in its thioester form (this fragment is termed UbN or Ub1N, Ub2N, Ub3N and Ub4N in the text below), and a C-terminal fragment containing (this fragment is termed UbC or Ub1C, Ub2C, Ub3C and Ub4C in the text below), by a Native Chemical Ligation of the N-fragments with the C-fragments to obtain the complete monomer. If needed, these Ub monomers are designed to include unnatural amino acids, as detailed further below.

The term "ligating" with regard to the Ub thioester unit and the Ub unit, as used herein, refers to a ligation reaction between two Ub fragments or Ub units (either mono- or poly-Ub) and includes both linear (sequential) ligation and convergent ligation.

The ligation is preferably conducted under the following conditions:

Temperature ranging from 36 to 38° C., pH ranging from 6.5 to 7.5.

The ligation is generally conducted in the presence of a ligation agent, such as thiol additives like thiophenol, benzyl mercaptan, Sodium 2-mercaptoethanesulfonate (MesNa), and related alkyl and aryl thiols.

In particular, the ligation according to the present invention refers to a trans-thio-esterification reaction of the 1,2-thioamine-containing first ubiquitin unit with a second Ub thioester unit, followed by S—N acyl transfer.

In order for the ligation to take place with the Ub-thioester unit Ubm, the Ubq unit must contain at least one un-protected nucleophilic 1,2 thioamine containing amino acids.

The term "1,2 thioamine containing amino acid" refers to amino acids containing the 1,2 thioamine group. Examples of 1,2 thioamine containing amino acids include, but are not limited to, mercaptolysine and various modifications thereof, as well as to the products obtained from the reaction of Cys amino acid with one of the following: glutamic acid, aspartic acid, Ser, Thr and Lys.

Preferably, the unprotected 1,2 thioamine containing amino acid is a mercaptolysine amino acid or a derivative thereof, such as an N-methyl mercaptolysine.

Preferably, the protected 1,2 thioamine containing amino acid, contain the same 1,2-thioamine containing amino acid as described hereinabove, where preferably it is important that the thiol protecting group will not be demasked before the SPPS is completed, namely that when using Boc-SPPS, after the removal of alloc under palladium catalysed reaction conditions, treatment with HF or TFMSA will not remove the thiol protection. Thus, the number of suitable thiol protecting group for the 1,2 thioamine containing amino acid, according to the present invention, is very limited.

Some examples of suitably-protected 1,2 thioamine containing amino acid have been described in the parallel patent application having the reference number 11-078 and are presented in Scheme 1 below. These include, but are not limited to, 1e, 1b and 1d (i.e., the protection groups being: thiazolidine (Thz) for 1b, P-hydroxymercuribenzoate (PMB) for 1d and t-Bu for 1e).

Scheme 1

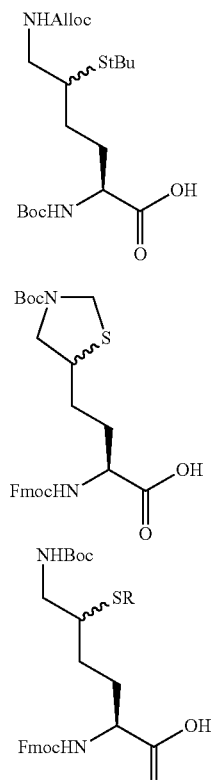

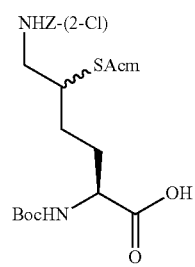

Thus, according to preferred embodiments of the reaction, the protecting group of the thiol in the 1,2 thioamine containing amino acid is selected from: t-Butyl, thiazolidine (Thz) and p-hydroxymercuribenzoate, Acetamido, Benzamido, Acetyl, Hqmc, 2-Nitrobenzyl.

Most preferably, the protected 1,2 thioamine containing amino acid is a (Thz)-protected mercaptolysine.

The general structure of the is provided in Formula III below:

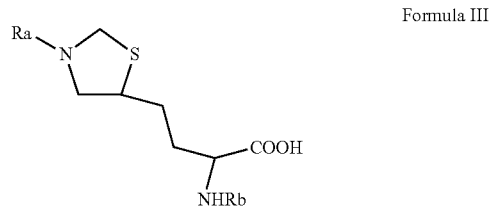

wherein Ra and Rb are independently either hydrogen or nitrogen protecting groups.

Examples of amine protecting groups include, but are not limited to, the following: 1) acyl types such as formyl, trifluoroacetyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boa), di-tert-butyl dicarbonate (Boc), ethoxycarbonyl, diisopropylmethoxycarbonyl, and allyloxycarbonyl; and 4) cyclic alkyl carbamate types such as cyclopentyloxycarbonyl and adamantyloxycarbonyl. Other Amine protecting groups are known to a person skilled in the art.

Preferably, Ra and Rb are either hydrogen or the protecting groups Boc or Fmoc.

The Ub monomer or "building block" Ubq used as described hereinabove in obtaining the various poly-Ubs is a ubiquitin monomer or ubiquitin thioester modified by the 1,2 thioamine "handle". Scheme 2 below shows the steps in preparing various modified Ubs, wherein the K amino acid replaced by the protected-Thz mercaptolysine amino acid K*, from two fragments UbC and UbN-SR, whereas one route (on the left) applies when the modification (K→K*) is in positions 6, 11, 27, 29 or 33 and the second route (on the right) applies when this modification is in positions 48 or 63.

In the former, the modified amino acid is incorporated in the UbN-SR fragment, and in the latter, the modified amino acid is incorporated in the UbC fragment.

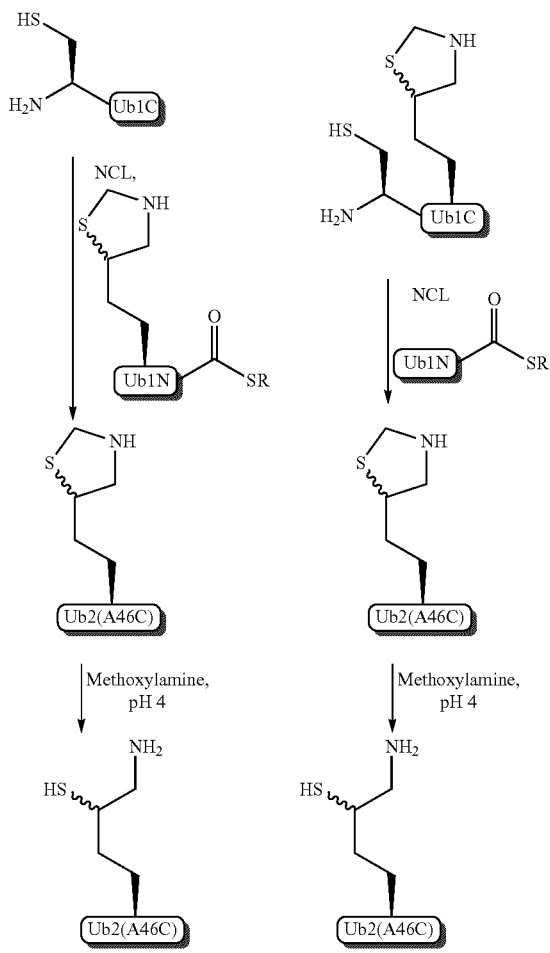

As can be seen in the Examples which follow, modified ubiquitin proteins were chemically prepared according to the general synthetic process described herein, replacing the natural lysines in the ubiquitin structure, by the modified Thz-protected δ-mercaptolysine (1b), prepared according to the process outlined in parallel patent application having the reference number 11-078. After the ligation between the two ubiquitin fragments took place, the protected mercaptolysine was deprotected by the addition of methoxylamine. Finally, desulfurization was effected to turn the Cysteine into Alanine.

This afforded a series of 7 modified ubiquitin proteins, termed $Ub_{k6}$, $Ub_{k11}$, $Ub_{k27}$, $Ub_{k29}$, $Ub_{k33}$, $Ub_{k48}$ and $Ub_{k63}$, whereas the number next to the letter k indicates the position where the lysine was initially replaced by the Thz-protected mercaptolysine (1b).

In order to obtain the $Ub_{k6}$, $Ub_{k11}$, $Ub_{k27}$, $Ub_{k29}$, $Ub_{k33}$ modified peptides, the N-terminus fragment thioesters thereof, $UbN_{K33}$-SR, $UbN_{K29}$-SR, $UbN_{K27}$-SR, $UbN_{K11}$-SR and $Ub_{NK6}$-SR, prepared according to section (a) hereinabove were ligated with unmodified C-fragment UBC, prepared according to section (b) hereinabove.

In order to obtain the $Ub_{k48}$ and $Ub_{k63}$ modified peptides, the C-terminus fragments thereof, $UbC_{K48}$ and $UbC_{K63}$, prepared according to section (b) hereinabove were ligated with unmodified N-fragment UBN, prepared according to section (a) hereinabove.

As used herein, the term "thioester", interchangeably used with the term "thioloester", refers to a moiety represented by —COSR, often connected to a peptide.

The term "Ub thioester" or "Ub in its thioester form" may be represented as "Ub-α-COSR" or "Ub-SR". The R group in this case generally be an alkyl or aryl, optionally substituted ones, including derivatives thereof, 1-4 amino acids or derivatives thereof, preferably wherein the R group is selected such that the peptide-α-COSR is an activated thioester. Preferably, the R may be include 1-15 C functionalized alkyl, straight or branched, 1-15 C aromatic structures.

The present invention is based on using Ub thioesters having m Ub monomers, m being an integer equalling 1 and above. Namely, the Ub thioester can be a mono-Ub thioester or a poly-Ub thioester.

While the current methods to prepare Ub-SRs are relying on either the use of the enzymatic machinery E1-E2 or on expressed protein technology, these approaches are limited mainly to natural amino acids modification, thereby inhibiting chemical manipulation of ubiquitin.

The chemical preparation of the Ub thioesters has now been provided by the present authors, and is disclosed in a patent application having the reference number 11-078, being co-filed on the same date as the instant application, claiming the same priority (provisional application No. 61/302,359) and entitled "A Process For The Preparation Of Ubiquitin Thioesters", which is incorporated by reference as if fully set forth herein.

Thus, the present invention encompassed Ub thioesters, being prepared both of natural Ub polypeptides, as well as on chemically synthesizing said Ub polypeptides, as described in said parallel patent application referenced 11-078.

The term "Chemically synthesizing" refers to the fact that the obtaining of the polypeptide or the polypeptide thioester is not conducted enzymatically or by gene expression, neither in vivo nor in vitro.

As explained hereinabove, in order to enable conducting sequential (linear) ligations, the Ub thioester must contain at least one protected 1,2 thioamine containing amino acids. The protected 1,2 thioamine group can then withstand an initial ligation between the Ub thioester Ubm-SR and the Ub unit, be activated upon removal of the protecting group to obtain a reactive, nucleophilic, 1,2-thioamine containing amino acid, that can be further ligated with yet another Ub thioester unit.

Indeed, as long as the ligation of the Ub thioester unit Ubm-SR and the Ub unit Ubq, does not yet form the requested poly-peptide having n Ub monomers, namely as long as the sum of q and m is still smaller than n, the existence of the protected 1,2-thioamine containing amino acid in the Ub thioester unit, is essential.

For example, if preparing a tri-Ub chain, in a two-step linear process (n=3, x=2), during the first step a Ub containing unprotected (nucleophilic) 1,2-thioamine containing amino acid (Ubq, q=1) reacts with a Ub-thioester containing a protected 1,2-thioamine containing amino acid (Ubm-SR, m=1, m+q=2<n=3), to obtain a di-Ub containing this protected 1,2-thioamine containing amino acid. In the second step, this protection is removed and the previously-obtained di-Ub containing this unprotected 1,2-thioamine containing amino acid (Ubq, q=2) is reacted with an additional Ub-thioester (Ubm-SR, m=1). However, at this stage (m+q=3=n), no protected 1,2-thioamine group is necessary in the thioester.

As noted hereinabove, if the Ub thioester contained at least one 1,2-thioamine containing amino acid (namely, p is 1 and above), de-masking of this protection from the ligation product is needed before entering additional ligations or additional chemical reactions The term "de masking" refers to the removal of the protecting group to "un mask" or activate the 1,2 thioamine group by a "demasking agent" also termed "de-protecting agent". In the ensuing examples, the demasking agent was methoxylamine. Other examples of de-protecting groups suitable for selective de-protection of the 1,2-thioamine group include, but is not limited to, Cu salts.

The native isopeptide linkage is finally obtained by a desulfurization.

The term "desulfurization" as used herein refers to the removal of the thio group from the linking group of the Ub thioester unit and the Ub unit forming the poly-Ub chain, to obtain an isopeptide linkage. In one embodiment, the desulfurization is conducted with a metal catalyst. Examples of suitable metal catalysts are selected from Raney nickel, platinum, palladium on carbon (Pd/C), $Ni_2B$, and $NiCl_2$, and $NaBH_4$. Additional details on the desulphurization process are provided in the experimental section below.

Since in nature, the known poly-Ubs are mostly di-Ub chains and tetra-Ub chains, it is of interest to conduct the process described herein to create poly-Ub chains containing 2, 3 or 4 Ub monomers (n=2, 3 or 4).

Thus, according to preferred embodiments of the invention, n is 2, 3 or 4.

However, for various research and other uses, longer chains can easily be prepared with the same process.

As noted hereinabove, this general synthetic route encompasses both sequential ligation and convergent addition, which is applicable mostly for large poly-Ub chains.

Thus, some useful examples of preparing di-, tri- and tetra-Ub chains, include the following combinations:

The process described herein, wherein n is 2, x is 0, m is 1 and q is 1, to obtain a di-ubiquitin in one step.

The process described herein, wherein n is 3, x is 0, to obtain a tri-ubiquitin in one step, whereas:
i) m is 1 (a Ub monomer thioester) and q is 2 (a di-Ub); or
ii) m is 2 (a di-Ub thioester) and q is 1 (a Ub monomer).

The process described herein, wherein n is 3, x is 1, and m is 1 (a Ub monomer thioester) in each step, to obtain a tri-ubiquitin in two steps.

The process described herein, wherein n is 4 and x is 0 to obtain a tetra-ubiquitin in one step, whereas:
i) m is 2 (a di-Ub thioester) and q is 2 (a di-Ub); or
ii) m is 1 (a Ub monomer thioester) and q is 3 (a tri-Ub); or
iii) q is 1 (a Ub monomer) and m is 3 (a tri-Ub thioester).

The process described herein, wherein n is 4 and x is 2, and m is 1 in each step (a Ub monomer thioester), to obtain a tri-ubiquitin in two steps.

It should be clarified that the linear preparation (sequential ligation) would be characterized in that the Ubm-SR would be a Ub monomer thioester, namely that m would be 1 in all steps, and the total number of steps (assuming starting from a Ubq monomer, q=1).

For example, the process is now detailed for obtaining a tetra-Ub chain, by both linear and convergent strategies:

1. By Linear strategy: Here three distinct ubiquitin (Ub) fragments are synthesized separately and are assembled one after the other. Thus, the first ubiquitin with C-terminus acid having 1,2 thioamine (such as mercaptolysine) at the suitable position of the Ub-chain (Ub1—with 1,2 thioamine "handle") will be ligated to the second ubiquitin chain synthesized as a C-terminus thioester having a protected 1,2 thioamine, (Ub2 (with protected 1,2 thioamine "handle")-SR), whereas the protected 1,2 thioamine "handle" can be Thz-protected mercaptolysine. After the termination of the ligation step, the protection group is removed from the 1,2 thioamine, for example by the addition of methoxylamine. The sequence of reaction is repeated with the resultant diubiquitin (Ub1-2 with 1,2 thioamine "handle") and another Ub2 (with protected 1,2 thioamine "handle")-SR to yield, upon removal of the protection, a nucleophilic tri-ubiquitin (Ub1-2-3 with 1,2 thioamine "handle"). This tri-ubiquitin is further ligated to a native ubiquitin thioester (Ub4-SR) to give tetra ubiquitin with sulphur atoms at the ligation centers.

In the final step, radical induced or metal catalyzed desulfurization technique furnishes the target tetra ubiquitin. This strategy can be used in the synthesis of all lysine linked tetraubiquitins, as well as for the synthesis of longer chains.

Scheme 3 shows the linear poly-ubiquitation process for an exemplary 4-unit Ub chain (tetramer), whereas Ub2, Ub3 and Ub4 are the Ub-thioester monomers:
Scheme 3
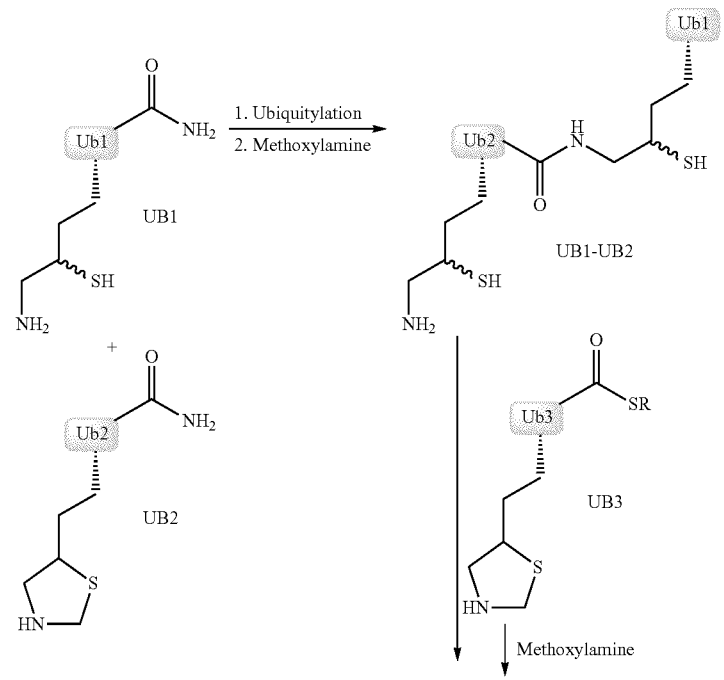
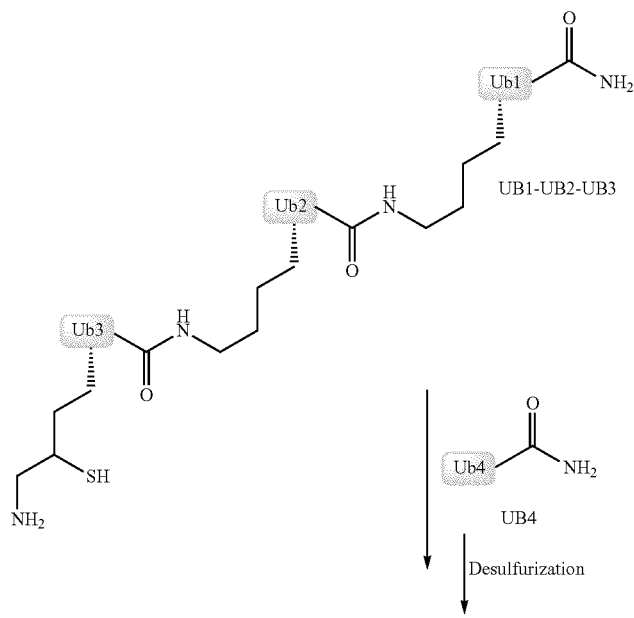

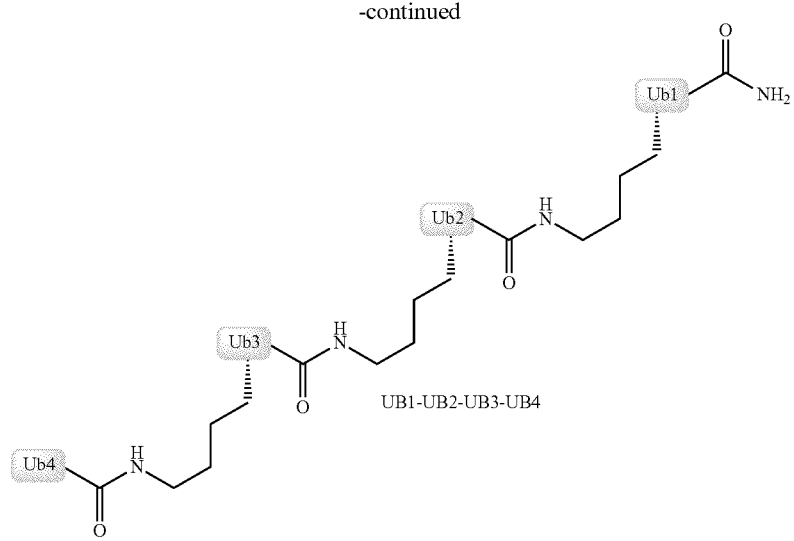

UB1-UB2-UB3-UB4

2. By Convergent strategy: This is another interesting and elegant route towards the synthesis of even-numbered ubiquitin chains. The advantage of having the even number of repeating is used by separately synthesizing two short ubiquitin chains of half the number of units as required in the final chain (for example synthesizing di-ubiquitins if tetra-ubiquitin is required), whereas one chain is in the form of a thioester and the other chain has an unprotected 1,2 thioamine group (such as mercaptolysine) at the desired position, according to the methods described hereinabove for the linear preparation of chains. These two chains are then ligated under NCL conditions to furnish the longer ubiquitin with sulphur moiety at the ligation junctions. Finally, radical/metal catalyzed desulfurization step was performed to furnish the required protein. Due to the cost efficiency and simplicity the convergent strategy is preferred. This strategy is useful for all types (K48, K63, K33, K29, K27, K11, K6) of tetra ubiquitin.

Scheme 4 shows the Convergent polyubiquitation process for an exemplary 4-unit Ub chain (tetramer), wherein Ub2 and Ub4 are prepared as thioesters, such that the Ub2 thioesters contains a Thz-protected mercaptolysine. U3 is prepared as a latent-thioester functionality-attached to a Ub peptide containing a Thz-protected mercaptolysine, as detailed in Example 7 in parallel patent application having the reference number 11-078, as provided hereinabove.

Scheme 4

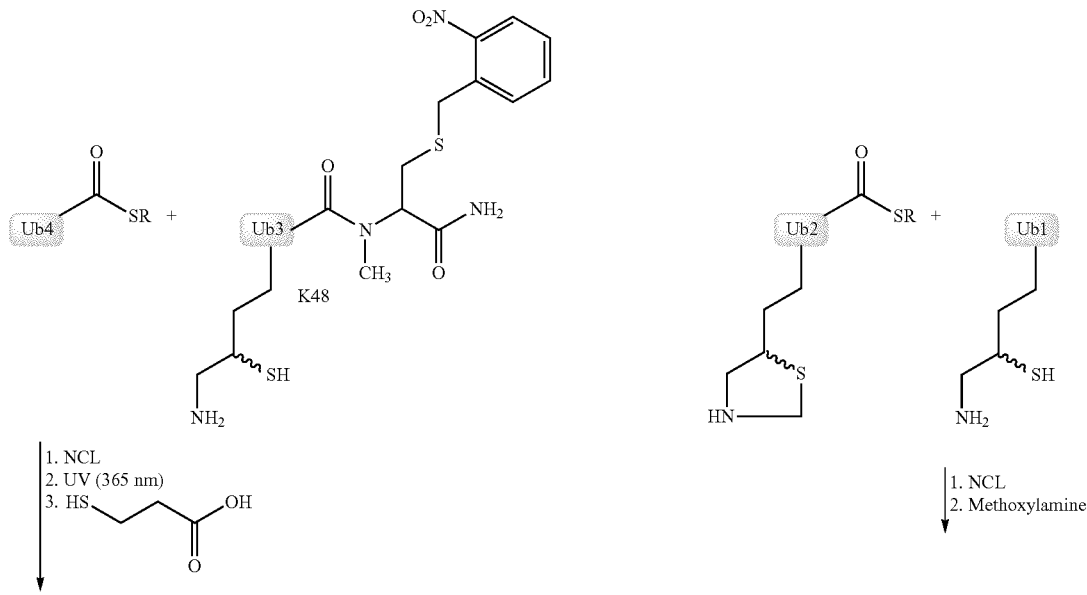

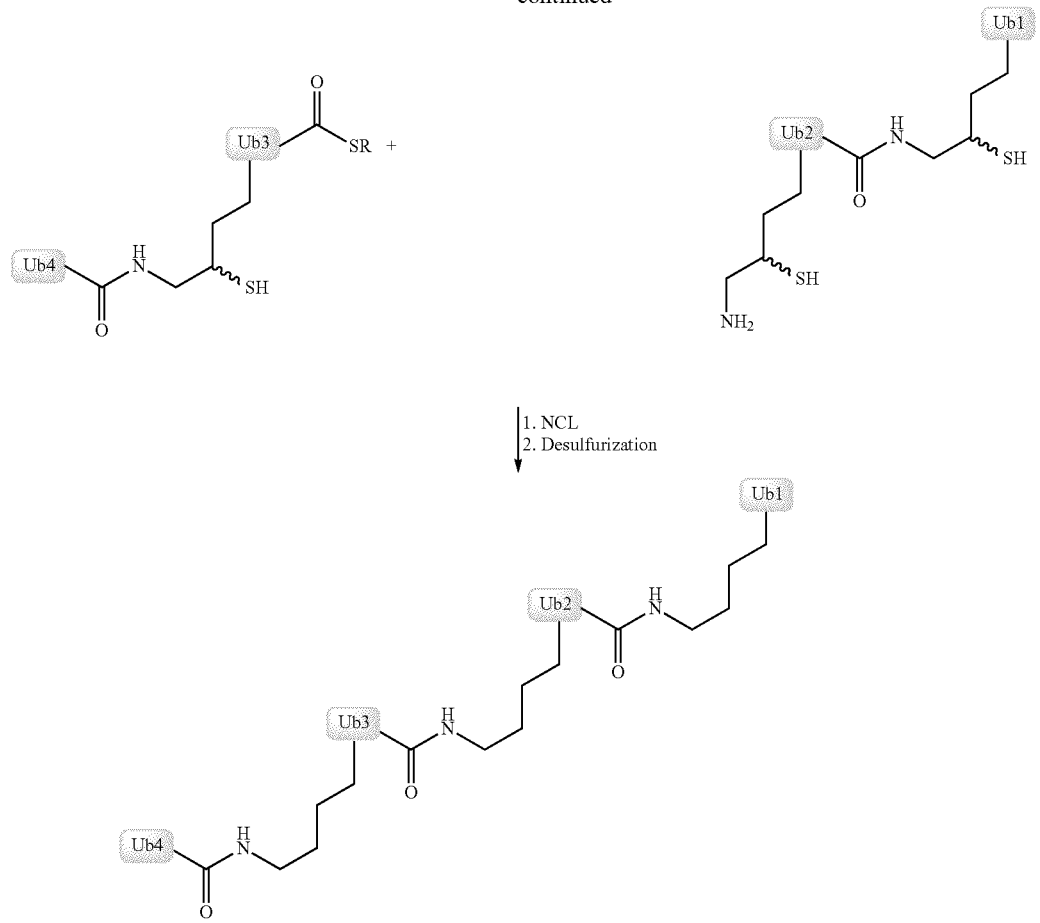

As can be seen in Scheme 2, The ubiquitin chain Ub1$_{K48}$-Ub2$_{k48}$ with C-terminal acid and suitably positioned mercaptolysine (here at lysine 48) was ligated with another ubiquitin chain with C-terminus thioester and having protected mercaptolysine (K48). After the completion of ligation the protecting group was unmasked to avail the K48 linked diubiquitin, necessary as nucleophile for the ligation in the next step.

The preparation of Ub3-Ub4-thioester chain, necessary as electrophile for the ligation in the next step, is based on preparing a Ub3 chain as photo-switchable thioester at the C-terminus and having mercaptolysine (K48) while Ub4 was synthesized as ubiquitin thioester in its native form. These two chains were then ligated under NCL conditions and the photolabile protection at the C-terminus of Ub3 was removed and converted to MPA-thioester form of Ub$_{K48}$-Ub4 (electrophile) using 20% MPA.

The nucleophile in the form of Ub1$_{K48}$Ub2$_{K48}$ was ligated with electrophile Ub3$_{K48}$Ub4-SR for 30 hours to yield K48 linked tetraubiquitin with sulphur atoms attached to the ligation sites. Desulphrization was conducted to obtain the tetraubiquitin in its final form.

As has been shown hereinabove, the inventors have now provided an easy and versatile chemical process to prepare poly-ubiquitins.

Since this is the first chemical synthesis of such poly-Ub units, it is now possible, using the new process, to obtain poly-Ubs containing unnatural amino acids, such as the mercaptolysine amino acid.

Thus, according to preferred embodiments of the invention, there is now provided a process to obtain a poly-ubiquitin chain Ubn containing at least one unnatural amino acid, whereas in one or more of the (x+1) steps of the process, at least one of the ubiquitin Ubq and/or the ubiquitin thioester Ubm-SR contain this at least one unnatural amino acid.

Furthermore, according to yet another aspect of the invention, there is now provided a use of the process described hereinabove to prepare poly-ubiquitin chains.

According to preferred embodiments of the invention, there this use is for the preparation of di-ubiquitins, tri-ubiquitins or tetra-ubiquitins.

In another preferred embodiments of the invention, there this use is for the preparation of a natural poly-ubiquitin, a modified poly-ubiquitin, a labeled poly-ubiquitin, or a poly-ubiquitin containing at least one unnatural amino acid.

Consequently, according to yet another aspect of the invention, there is now provided a poly-ubiquitin chain Ubn, comprising n ubiquitin monomers linked by isopeptide bonds, n being an integer larger than 1, prepared according to the process described herein.

The process described herein allows, for the first time, designing and preparing a variety of modified poly-Ubs, in particular poly-Ubs containing unnatural amino acids, such as labeled amino acids and additional modifications, as can be envisioned by a person skilled in the art.

In particular, according to yet another aspect of the invention, there is now provided a poly-ubiquitin chain Ubn, comprising n ubiquitin monomers linked by isopeptide bonds, n being an integer larger than 1, this Ub chain containing at least one unnatural amino acid.

For example, according to a preferred embodiment of the invention, there is provided a ubiquitin chain containing one or more ubiquitin monomers, wherein one or more of these contain a Thz-protected-mercaptolysine replacing one or more of the 7 lysine natural lysines in each Ub chain. These are often building blocks in the preparation of longer ubiquitin chains.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

MATERIALS AND ANALYTICAL METHODS

Materials:
The meaning of the abbreviations used in the description and the claims is as outlined in the table below:
Fmoc 9-Fluorenylmethoxycarbonyl-
Boc t-Butoxycarbonyl-
DIEA Diisopropylethylamine
TFA Trifluoraceticacid
DMF N,N'-Dimethylformamide
HBTU O-Benzotriazole N,N,N',N'-tetramthyl-uronium-
HOBt 1-Hydroxybenzotriazole
DBU 1,8-Diazabicyclo[5.4.0]undec-7-ene
HATU O-(7-Azabenzotriazol-1-yl)-N,N,N',N'-tetramethyluronium-hexafluoro-phosphate
MEI Methyl iodide
TBAF Tetrabutylammonium Fluoride
MPA 3-mercaptopropionic acid
DTT Dithiothreitol
Tris Tris-(hydroxymethyl)aminomethane
THF Tetrahydrofuran
NaHMDS Sodium Hexamethyldisilazane DMF was purchased in biotech grade. Commercial reagents were used without further purification.

Resins, protected and unprotected amino acids, and coupling reagents (HBTU, HOBt) were purchased from Novabiochem.

Buffer B is acetonitrile with 0.1% v/v TFA and buffer A is water with 0.1% v/v TFA.

Methanol, triethylamine, THF, ether were purified and dried before use.

The n-hexane used was the fraction distilling between 40-60° C.

Natural ubiquitin, which was used for comparison (from bovine erythrocytes) was purchased from Sigma.

Ubiquitin thioesters and protected 1,2 thioamines (such as Thz-protected mercaptolysine) were prepared according to the process described in a patent application being co-filed on the same date as the instant application, having the reference number 11-078PCT, claiming the same priority (provisional application No. 61/302,359) and entitled "Chemical Preparation of Ubiquitin Thioesters and Modifications Thereof", which is incorporated by reference as if fully set forth herein.

All other chemicals were purchased from either Aldrich and/or Fluka.

Note: Throughout this specification amino acid residues will be denoted by the three-letter abbreviation or single-letter code as follows:
Three-Letter One-Letter Amino Acid Abbreviation Symbol
Alanine Ala A
Arginine Arg R
Asparagine Asn N
Aspartic Acid Asp D
Cysteine Cys C
Glutamine Gln Q
Glutamic Acid Glu E
Glycine Gly G
Histidine His H
Isoleucine Ile I
Leucine Leu L
Lysine Lys K
Methionine Met M
Phenylalanine Phe F
Proline Pro P
Serine Ser S
Threonine Thr T
Tryptophan Trp W
Tyrosine Tyr Y
Valine Val V General Synthetic Methods to Prepare Ubiquitin:
Ub proteins (termed hereinbelow Ub1, Ub2, Ub3 and Ub4) were prepared from two peptide segments obtained from separate SPPS reactions: an N-terminal fragment containing amino acids 1-45, in its thioester form (this fragment is termed UbN or Ub1N, Ub2N, Ub3N and Ub4N in the text below), and a C-terminal fragment containing amino acids 46-76 (this fragment is termed UbC or Ub1C, Ub2C, Ub3C and Ub4C in the text below). If needed, one or more of the amino acids are modified by a unnatural amino acid during the SPPS stage (for example replacing one or more of the 7 natural lysines with an analogue, such as a protected or non-protected mercaptolysine; or—replacing natural Alanine amino acids by Cysteine amino acids).

The two segments were coupled using native chemical ligation (6M Gn.HCl, pH 7 in presence of 2% thiophenol). Desulfurization was used to turn any un-natural Cysteine into an Alanine amino acid.

0.2 M Methoxylamine was used to unmask the Thz-protected mercaptolysine.

SPPS was carried out manually in syringes, equipped with teflon filters, purchased from Torviq or by using an automated peptide synthesizer (CS336X, CSBIO). If not differently described, all reactions were carried out at room temperature.

All other reactions were carried out in oven-dried glassware under dry argon.

Instrumental Data:
Mass spectrometry was conducted using LCQ Fleet Ion Trap (Thermo Scientific).

Analytical HPLC was performed on a Thermo instrument (Spectra System p4000) using an analytical column (Jupiter 5 micron, C18/C4, 300 A 150×4.6 mm) and a flow rate of 1.2 mL/min.

Preparative HPLC was performed on a Waters instrument using semi-preparative column (Jupiter 10 micron, C4, 300 A, 250×10 mm) and a flow rate of 5 mL/min as well as a preparative column (Jupiter 5 micron, C18/C4, 300 A, 250×22.4 mm) and a flow rate of 25 mL/min.

$^1$H (500 MHz) and $^{13}$C (125 MHz) NMR spectra were recorded using CDCl$_3$ as a solvent. Chemical shifts are reported in d units (ppm) with reference to TMS as an internal standard, and J values are given in Hz. $^1$H and $^{13}$C-NMR spectra were recorded on a Bruker AMX-500 MHz spectrometer.

Flash column chromatography was carried out with silica gel (60-100 mesh).

Analytical thin-layer chromatography (TLC) was performed using thin layer chromatography on pre-coated plates (0.25 mm, silica gel 60 F254).

Compound spots were visualized by UV light (254 nm) and were stained with citric ammonium molybdate.

Circular Dichroism (CD) Analysis:

Samples preparation: The diubiquitin analogues were dissolved in 6 M Gn.HCl 200 mM phosphate buffer (pH 7.86) 5% of the total volume and diluted with 50 mM Tris buffer (pH 7.54). The Gn.HCl buffer was then extracted by Amicon® Ultra-0.5 10KDa MWCO (Millpore). The exact final concentration of each protein solution was determined using Pierce® BCA Protein Assay Kit (Thermo scientific) and diluted to a final concentration of 10 µM.

The CD measurements were carried out on a Jasco-815 CD spectropolarimeter, at 25° C., by using a quartz cell with 1.0 mm path length and 16 second averaging times. The CD signals, which resulted from the buffer were subtracted from the spectrum of each sample. Data was converted to ellipticity (θ in deg*cm2*dmol−1) according to the equation: [θ]molar=θobs/(nlc), where θobs is the CD signal in degrees, n is the number of peptide bonds, 1 is the path length in centimeters, and c is the concentration in decimoles per cm$^3$.

Enzymatic Hydrolysis of Di-Ub Chains:

The diubiquitin analogues were dissolved in 6 M Gn.HCl 200 mM phosphate buffer (pH 7.86) 5% of the total volume and diluted with 50 mM Tris buffer (pH 7.54). The Gn.HCl buffer was then extracted by Amicon® Ultra-0.5 10 KDa MWCO (Millpore). 0.1 mM EDTA was added and the exact final concentration of each protein solution was determined using Pierce® BCA Protein Assay Kit (Thermo scientific) and diluted to a final concentration of 10 µM. Stock solution of the Isopeptidase T, human recombinant (BostonBiochem) (1 µM) was prepared by diluting 25 µg of the enzyme in 50 mM Tris buffer (pH 7.54) containing BSA (1 mg/mL) and 0.5 mM DTT. The enzymatic assay was initiated by incubating each substrate (5 µM) with Isopeptidase T (10 nM) for 5 minutes at 37° C. Enzyme activity was detected by analytical HPLC using C4 column, 5-55% B over 35 minutes. Each experiment was repeated three times and averaged for each case. The percent of hydrolysis was determined from the integration ratio of the Ub to di-Ub.

Example 1

Preparation of Ubiquitin Peptides Modified by Thz-Protected Mercaptolysine

Ub$_{k6}$, Ub$_{k11}$, Ubk27, Ubk29, Ubk33, Ubk48 and Ubk63 a) Obtaining the Respective N-Terminus Fragments as Thioesters

UbN-SR:
LQIFVKTLTGKTITLEVEPSDTIENVKAKIQDKEGIPPDQQRLIF-SR

UbN$_{K33}$-SR:
LQIFVKTLTGKTITLEVEPSDTIENVKAKIQDK*EGIPPDQQRLIF-SR

UbN$_{K29}$-SR:
LQIFVKTLTGKTITLEVEPSDTIENVKAK*IQDKEGIPPDQQRLIF-SR

UbN$_{K27}$-SR:
LQIFVKTLTGKTITLEVEPSDTIENVK*AKIQDKEGIPPDQQRLIF-SR

UbN$_{K11}$-SR:
LQIFVKTLTG K*TITLEVEPSDTIENVKAKIQDKEGIPPDQQRLIF-SR

UbN$_{K6}$-SR:
LQIFVK*TLTGKTITLEVEPSDTIENVKAKIQDKEGIPPDQQRLIF-SR

K* = Thz-protected mercaptolysine (1b)

I. Peptide N-Fragment Thioester Synthesis by SPPS:

Rink amide resin (0.2 mmol/g, 0.1 mmol scale, 500 mg) was used for the synthesis of the N-terminus peptide fragments.

The first two amino acids, (i.e. 3-Fmoc-4-diamino benzoic acid (Fmoc-Dbz), and Phe), were each double coupled manually for 1 hour using HBTU/HOBt in 4 fold excess of the initial loading of the resin. DIEA was used in 10-fold excess. Fmoc deprotection was achieved by treatment of the resin with 20% piperidine.

The remaining amino acids were coupled using the peptide synthesizer as previously described. The last amino acid was coupled in its Boc protected form. The Thz-protected δ-mercaptolysine (1b), prepared according to the process outlined in parallel patent application having the reference number 11-078, was manually coupled at position 33, 29, 27, 11 and 6 for UbN$_{K3}$3, UbN$_{K29}$, UbN$_{K27}$, UbN$_{K11}$, and Ub$_{NK6}$ respectively, using 2 eq of this residue to the resin initial loading. The coupling was performed for 2 hours, followed by analytical cleavage to ensure complete coupling. Met1 in ubiquitin was replaced with Leu1 to avoid oxidation during synthesis and handling (Leu1 ubiquitin has full biological activity and has no effect on structure).

II. On Resin Activation:

After peptide elongation, the resin was washed with CH$_2$Cl$_2$ and a solution of p-nitrophenylchloroformate (100 mg, 5 eq) in 10 mL of CH$_2$Cl$_2$ was added and shaken for 1 hour at RT. The resin was washed with CH$_2$Cl$_2$ (3×5 mL), and DMF (3×5 mL). To the washed resin, a solution of 0.5 M DIEA in DMF (5 mL) was added and shaken for additional 30 minutes. The resin was washed using DMF (3×5 mL).

III. Cleavage and Purification:

The procedure used for Ub1C was followed.

IV. Thioesterification:

The crude peptide was dissolved in 0.2 M phosphate buffer (pH ~7) containing 6 M Gn.HCl to a final concentration of ~3 mM, followed by the addition of 5% (v/v) methylmercaptopropionate (MPA). The solution was kept at RT for 20 minutes and purified by preparative RP-HPLC using a gradient of 10-60% B over 30 minutes (buffer A: 0.1% TFA in water; buffer B: 0.1% TFA in acetonitrile) to afford the corresponding thioester in ~30% yield. The analysis confirmed obtaining the desired products.

b) Obtaining the Respective C-Terminus Fragments

UbC: CGKQLEDGRTLSDYNIQKESTLHLVLRLRGG

UbC$_{K63}$: CGKQLEDGRTLSDYNIQK*ESTLHLVLRLRGG

UbC$_{K48}$: CGK*QLEDGRTLSDYNIQKESTLHLVLRLRGG

K* = Thz-protected mercaptolysine (1b)

I. Peptide Synthesis

The synthesis of peptides UbC, UbC$_{K63}$, UbC$_{K48}$ were carried out on preloaded Fmoc-Gly-Wang resin (0.66 mmol/g, 0.1 mmol scale). The peptide synthesis using the peptide synthesizer was carried out in presence of 4 eq of amino acid, 10 eq of DIEA and 4 eq of HBTU/HOBt to the initial loading of the resin. The coupling was kept for 1 hour and Fmoc-deprotection was achieved using 20% piperidine with 5/10/5 minutes cycles. Fmoc-Asp(OMpe)-OH was used to minimize aspartimide formation. The Thz-protected δ-mercaptolysine (1b), prepared according to the process outlined in parallel patent application having the reference number 11-078, was manually coupled at position 63 for Ub1C$_{K63}$ and at position 48 for Ub1C$_{K48}$ using 2 eq of this residue and HATU as coupling reagent. The coupling was performed for 2 hours, followed by analytical cleavage to ensure complete coupling.

II. Cleavage from the Resin:

A mixture of TFA, triisopropylsilane and water (95:2.5:2.5) was added to the dried peptide-resin and the reaction mixture was shaken for 2 hours at RT. The resin was removed by filtration and was washed with TFA (2×2 mL). To precipitate the peptide, the combined filtrate was added drop-wise to a 10-fold volume of cold ether, centrifugation, decanting of ether, followed by dissolving the residue in acetonitrile-water and lyophilization.

HPLC purification afforded the corresponding peptide fragments in ~21% yield (~70 mg). The analytical analysis was carried out on a C4 analytical column using a gradient of 5-45% B over 30 minutes. A similar gradient was used for the preparative HPLC. The analysis confirmed obtaining the desired products.

C) Obtaining Ub$_{k6}$, Ub$_{k11}$, Ub$_{k27}$, Ub$_{k29}$, Ub$_{k33}$, Ub$_{k48}$ and Ub$_{k63}$ by Native Chemical Ligation (NCL)

In a typical ligation UbC, (5 mg, 1 eq) and UbN (8.2 mg, 1.1 eq), were dissolved in 720 μL (2 mM) of 6 M Gn.HCl, 200 mM phosphate buffer pH ~7.0. To this solution 14 μL each of benzylmercaptan and thiophenol were added and incubated for 7 hours at 37° C. Subsequently, the mixture was treated for 12 hours at 37° C. with methoxylamine (0.2 M, 12 mg) at pH 4 and TCEP (30 eq) to unmask the δ-mercaptolysine. The reaction was followed using an analytical C4 column and a gradient of 5-25-50% B over 45 min. For preparative HPLC a similar gradient was used to afford the ligation product in ~30% yield (~4 mg).

In particular:

In order to obtain the Ub$_{k6}$, Ub$_{k11}$, Ub$_{k27}$, Ub$_{k29}$, Ub$_{k33}$ modified peptides, the N-terminus fragment thioesters thereof, UbN$_{K33}$-SR, UbN$_{K29}$-SR, UbN$_{K27}$-SR, UbN$_{K11}$-SR and Ub$_{NK6}$-SR, prepared according to section (a) hereinabove were ligated with unmodified C-fragment UBC, prepared according to section (b) hereinabove.

In order to obtain the Ub$_{k48}$ and Ub$_{k63}$ modified peptides, the C-terminus fragments thereof, UbC$_{K48}$ and UbC$_{K63}$, prepared according to section (b) hereinabove were ligated with unmodified N-fragment UBN, prepared according to section (a) hereinabove.

In order to prepare unmodified Ub, the unmodified C-terminus fragment UbC, prepared according to section (b) hereinabove was ligated with unmodified N-fragment UBN, prepared according to section (a) hereinabove.

Example 2

Preparation of All Di-Ubiquitin Chains

General Procedure for Ligation:

In a typical ligation a ubiquitin peptide modified by mercaptolysine, as prepared according to Example 1 hereinabove (Ub1$_k$, 2.8 mg, 1 eq) and an unmodified ubiquitin thioester, prepared according to parallel patent application having reference number 11-078, (Ub2-SR, 2.8 mg, 1 eq), were dissolved in 162 μL of M Gn.HCl, 200 mM phosphate buffer pH ~7.0. To this solution 3 μL each of benzylmercaptan and thiophenol were added and incubated for 24 hours at 37° C. The reaction was followed using a C4 analytical column using a gradient of 5-25-50% B over 45 minutes. Preparative RP-HPLC was performed on a Waters instrument using a semi-preparative column (Jupiter 5 micron, C4, 300 A, 250× 10 mm) to afford the ligation product in ~40% yield (2.2 mg).

General Procedure for Desulfurization:

Raney Nickel was prepared as reported by Yan and Dawson. A solution of 2.5 mg of the ligated product in 1 mL of 0.1 M phosphate buffer containing 6M Gn.HCl, pH 6, was added 10 mM tris(carboxyethyl)phosphane hydrochloride (TCEP). The reaction was followed using an analytical C4 column and a gradient of 5-25-50% B over 40 minutes, which indicated a complete reaction after 16 hours. Preparative RP-HPLC was performed on Waters instrument using an analytical column (Jupiter 5 micron, C4, 300 A, 150×4.6 mm) to afford the desulfurized product in ~60% yield (1.5 mg).

To assemble all di-Ub analogues, seven parallel ligation reactions were carried out between each Ub1$_k$ analogue and the unmodified Ub2-SR under the NCL conditions described above. 24 hours were needed for completion of the ligation. The desired products were obtained in 35-40% isolated yield.

In a separate experiment, the desulfurization of the two Cys in the Ub molecules to their original Ala46 was conducted along with the removal of the thiol handle from the δ-mercaptolysine. However, this resulted in incomplete desulfurization. However, by applying the H$_2$/Raney Nickel conditions in the presence of TCEP, a complete desulfurization was achieved after 14-16 hours, and a mass decrease of 96 Da was observed, as expected for the loss of three sulfur atoms. Thus, all di-Ub analogues were desulfurized using this condition to give the desired products (Ub$_{K6}$-Ub, Ub$_{K11}$-Ub, Ub$_{K27}$-Ub, Ub$_{K29}$-Ub, Ub$_{K33}$-Ub, Ub$_{K48}$-Ub, Ub$_{K63}$-Ub) in 55-60% isolated yield.

FIG. 1 depicts an exemplary MS spectra of a di-Ub prepared according to preferred embodiments of the present invention.

The CD spectra of all di-Ub chains were also measured and compared to the commercially available monoUb, demonstrating that each Ub monomer in these chains retains its globular fold, supporting correct folding of ubiquitin.

Each di-Ub (5 μM) was also treated with human isopeptidase T (IsoT), an enzyme responsible for the cleavage between adjacent Ub in the unanchored K48-linked chains in vivo (10 nM) in 50 mM Tris-HCl, pH 7.6, 37° C. The progress of each reaction was followed by HPLC monitoring the appearance of the hydrolyzed product i.e. Ub, which elutes earlier on the C4 column relative to the starting material and validated the reactivity of IsoT with the various di-Ubs.

Furthermore, the enzymatic activity of the UCH-L3 enzyme (a ubiquitin C-terminal hydrolase) was also evaluated, to determine its ability to hydrolyze the synthesized di-Ub chains. To test this, the UCH-L3 enzyme (1 μM) was incubated with each chain (10 μM) in 50 mM Tris-HCl, pH 7.6, 37° C. for 30 minutes, finding no detectable activity with any of these chains.

Example 3

Linear Preparation of Trimer-Ubiquitin Chains a) Preparation of Di-Ubiquitins Containing a Thz-Protected Mercaptolysine:

Di-ubiquitin was prepared according to Example 2, by replacing the unmodified ubiquitin thioesters Ub2-SR with a ubiquitin thioester modified with Thz-mercaptolysine in the selected ligation point $Ub2_k$-SR. This affords a di-ubiquitin, having a handle for another addition of a ubiquitin thioester.

Figure 2:
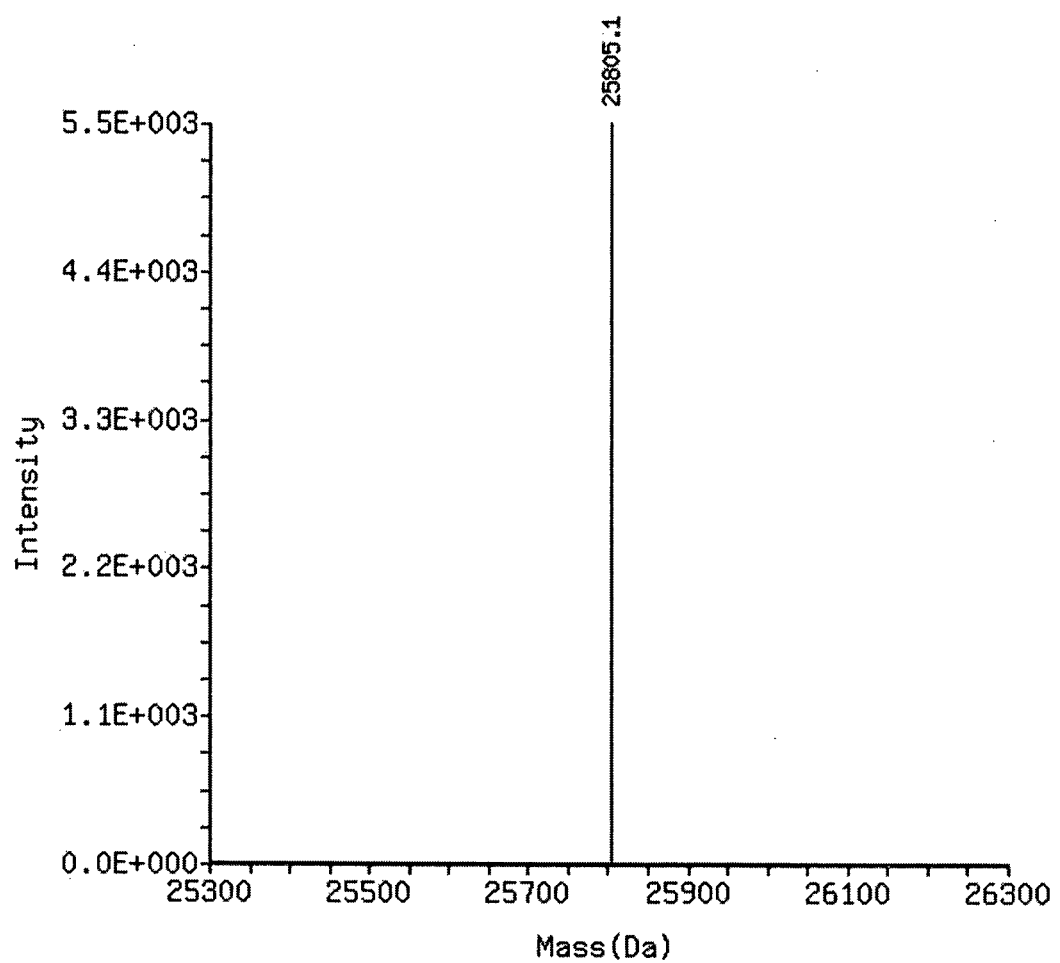
Figure 3:
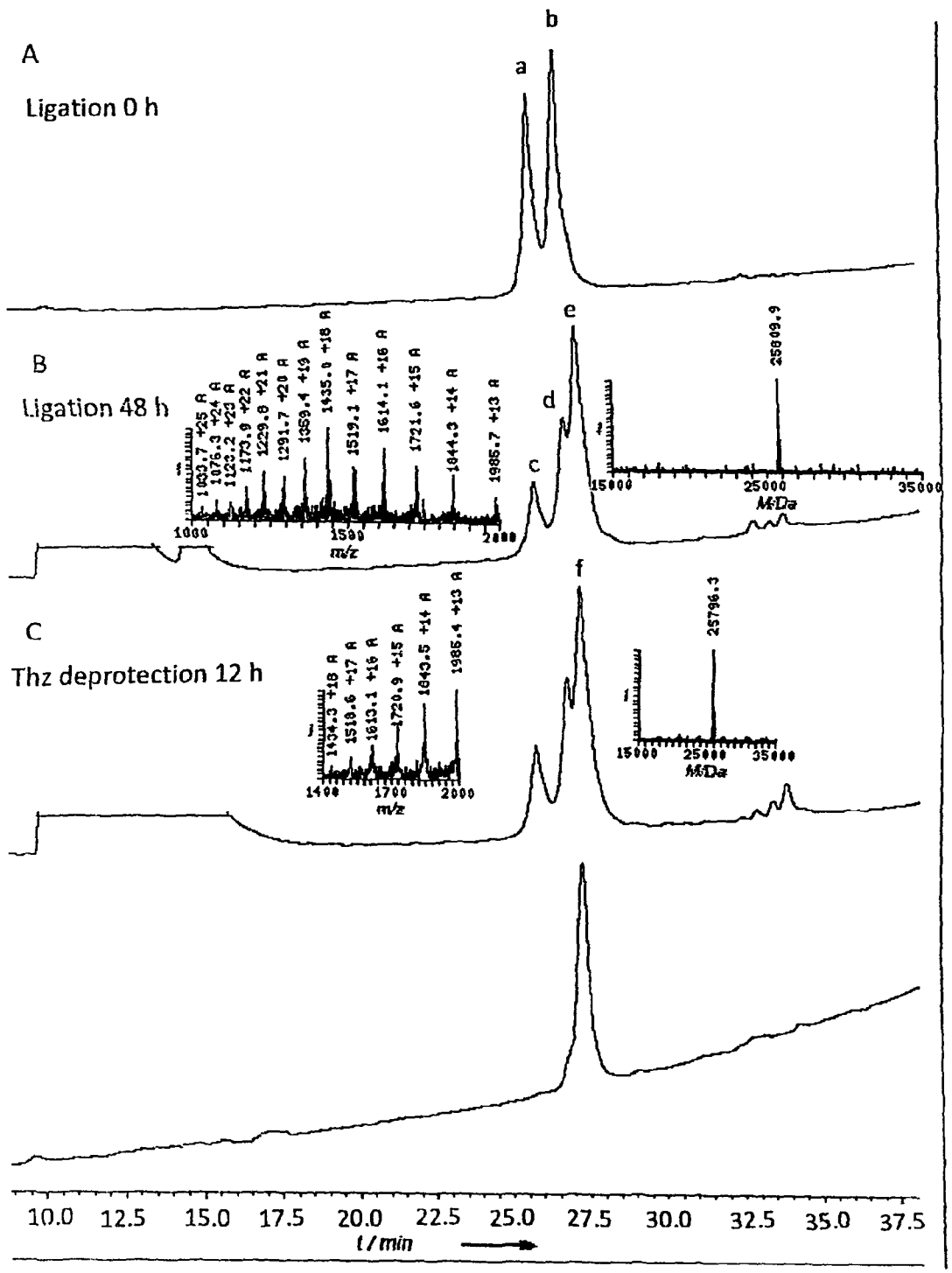

In particular, $Ub1_{K48}$, (5.2 mg, 1.1 eq) and $Ub2_{K48}$-SR (4.8 mg, 1 eq), were dissolved in 274 μL of 6 M guanidine.HCl, 200 mM phosphate buffer pH ~7.0. To this solution 5.5 μL each of benzylmercaptan and thiophenol were added and incubated for 24 h at 37° C. After 24 hours the reaction mixture was diluted with 274 μL of reaction buffer and incubated for additional 12 hours. Subsequently, the mixture was treated with methoxylamine (0.2 M, 9.2 mg) at pH 4 and TCEP (30 eq) to unmask the δ-mercaptolysine. The reaction was followed using an analytical column and a gradient of 5-15-40% B over 45 minutes. For preparative HPLC a similar gradient was used to afford the ligation product in 33% yield over two steps (~3.3 mg).

b) Ligation of Di-Ub with a Third Ub-SR:

According to one example, a $Ub1_{K48}$-$Ub2_{k48}$ (namely, where Ub1 and Ub2 are linked in position 48, and having another mercaptolysine in position 48 of the second Ub) prepared according to Example 2 was further ligated with unmodified Ub3-SR, prepared according to parallel patent application having the reference number 11-078, in 6 M Gn HCl pH 7 in presence of 2% (v/v) of thiophenol afforded UB1-UB2-Ub3 in 25% yield for the ligation followed by thiazolidine deprotection step. FIG. 2 depicts an exemplary MS spectra of the tri-Ub prepared according to preferred embodiments of the present invention. FIG. 3 depicts the HPLC and MS Analysis of at different stages of the process to obtain the tri-Ub according to preferred embodiments of the present invention: a) before ligation (ligation time=0 hours); b) after termination of the ligation (ligation time=48 hours), c) After removal of Thz-protection group (after 12 hours), and d) after completion of the reaction.

Example 4

Linear Synthesis of Tetra-Ubiquitin a) Preparation of Tri-Ubiquitins Containing a Thz-Protected Mercaptolysine:

Tri-ubiquitin was prepared according to Example 3, while replacing the unmodified ubiquitin thioester Ub3-SR with a ubiquitin thioester modified with Thz-mercaptolysine in the selected ligation point $UB3_k$-SR. This affords a tri-ubiquitin, having a handle for another addition of a ubiquitin thioester.

In one example, $Ub3_{K48}$SR, (2.2 mg, 1.5 eq) and $Ub1_{K48}Ub2_{K48}$ (3.0 mg, 1 eq), were dissolved in 70 μL of 6 M guanidine.HCl, 200 mM phosphate buffer pH ~7.0. To this solution 1.4 μL each of benzylmercaptan and thiophenol were added and incubated for 24 hours at 37° C. After 24 hours the reaction mixture was diluted with 70 of Gn.Hcl phosphate buffer and incubated for another 12 hours. Subsequently, the mixture was treated with methoxylamine (0.2 M, 2.4 mg) at pH 4 and TCEP (30 eq) to unmask the δ-mercaptolysine. The reaction was followed using an analytical column and a gradient of 5-15-40% B over 45 minutes. For preparative HPLC a similar gradient was used to afford the ligation product in 35% yield over two steps (~1.7 mg).

b) Ligation of Tri-Ub with a Fourth Ub-SR:

According to one example, a $Ub1_{K48}$-$Ub2_{k48}$-$Ub3_{k48}$ (namely, where Ub1, Ub2 and Ub3 are linked in positions 48, and further having another mercaptolysine in position 48 of the third Ub) prepared according to Example 3, was further ligated with unmodified Ub4-SR, prepared according to parallel patent application having the reference number 11-078.

Figure 4:
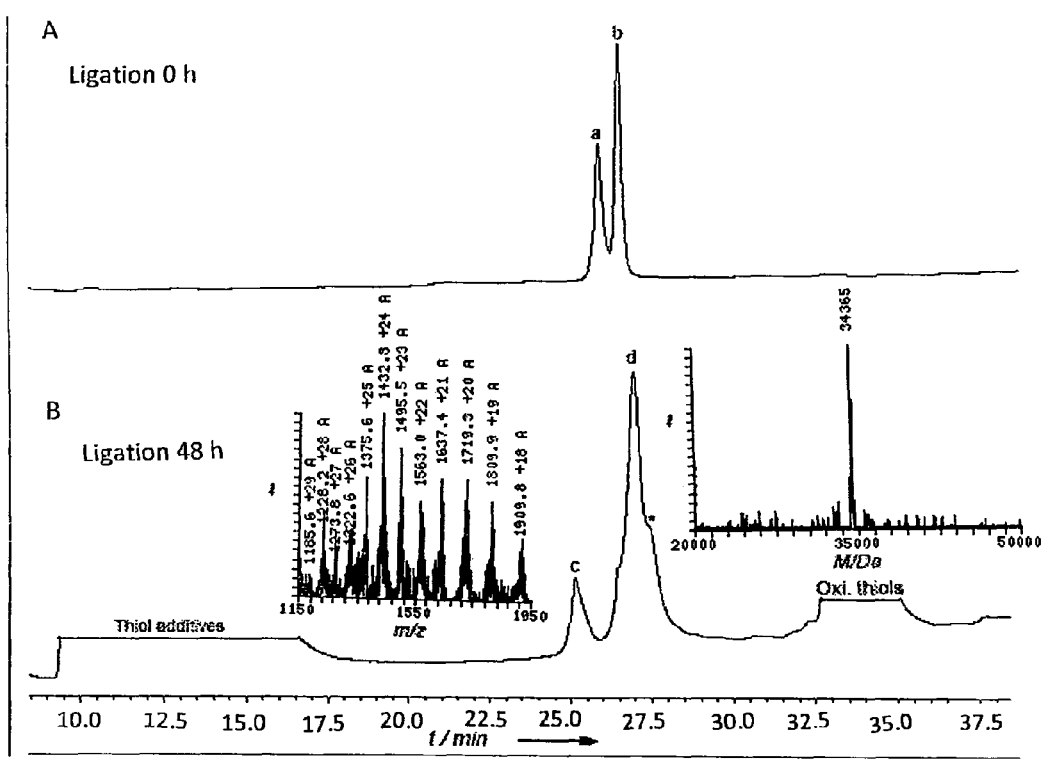

In particular, Ub4SR, (1.8 mg, 1.5 eq) and $Ub1_{K48}Ub2_{K48}Ub3_{K48}$ (3.7 mg, 1 eq), were dissolved in 71 μL of 6 M guanidine.HCl, 200 mM phosphate buffer pH ~7.0. To this solution 1.4 μL each of benzylmercaptan and thiophenol were added and incubated for 24 hours at 37° C. After 24 hours the reaction mixture was diluted with 70 of Gn.Hcl phosphate buffer and incubated for another 12 hours. The reaction was followed using an analytical column and a gradient of 5-15-40% B over 45 minutes. For preparative HPLC a similar gradient was used to afford the ligation product Ub1-Ub2-Ub3-Ub4 in 35% yield. FIG. 4 depicts the HPLC and MS Analysis of at different stages of the process to obtain the tetra-Ub according to preferred embodiments of the present invention: a) before ligation (ligation time=0 hours); and b) after termination of the ligation (ligation time=48 hours).

Example 5

Preparation of Tetramer-Ubiquitin Chains by the Convergent Strategy a) Synthesis of $Ub1_{K48}$-$Ub2_{K48}$ Chain:

The ubiquitin chain $Ub1_{K48}$-$Ub2_{K48}$ was prepared according to Example 4, step a.

b) Synthesis of $Ub3_{K48}$-Ub4 as Thioester:

I. Preparation of $Ub3_{k48}$-SR Precursor and Ub4-SR and Ligation Thereof:

$Ub3_{k48}$-SR precursor ($Ub3_{k48}$ attached to a latent thioester functionality) and Ub4-SR were both prepared according to parallel patent application having the reference number 11-078, whereas the mercaptolysine was unmasked in the $Ub3_{k48}$ but the reaction with the external thiol was not effected, thereby leaving the $Ub3_{k48}$ being linked to a latent thioester functionality. These two ubiquitins were then ligated under NCL conditions and the photolabile protection at the C-terminus of Ub3 (latent thioester functionality) was removed and converted to MPA-thioester form of $Ub3_{K48}$-Ub4 (electrophile) using 20% MPA.

In particular, $Ub3_{K48}$, (5.3 mg, 1.0 eq) and Ub4-SR (6.2 mg, 1.2 eq), were dissolved in 597 μL of 6 M guanidine.HCl, 200 mM phosphate buffer pH ~7.0. To this solution 11.9 μL each of benzylmercaptan and thiophenol were added and incubated at 37° C. After 24 hours the reaction mixture was diluted with 597 μL of reaction buffer and incubated for additional 12 hours. The reaction was followed using an analytical column and a gradient of 5-15-40% B over 45 minutes. For preparative HPLC a similar gradient was used to afford the ligation product in 34% yield over two steps (~4 mg). The Ligation was confirmed by mass spectrometry.

II. Conversion of $Ub4$-$Ub3_{K48}$ to $Ub4$-$Ub3_{K48}$-SR (Photolysis and Thiolysis):

Ub3-Ub4 obtained in the previous step (4.0 mg), were dissolved in 229 μL of photolysis buffer (6 M guanidine.HCl, 10 mM semicarbazide, 10 mM Vitamin C, 10 mM MPA, 200 mM phosphate buffer pH ~7.0). The reaction mixture was then irradiated at 360 nm for 1 hour and subsequently incubated with 20% MPA at 40° C. for 16 hours at pH 2. The reaction was followed using an analytical column C4 and a gradient of 5-15-40% B over 45 minutes. For preparative HPLC a similar gradient was used to afford the ligation product in 37% yield (~1.5 mg). The transformation to di-ubiquitin thioester was also confirmed by mass spectrometry.

c) Synthesis of Tetraubiquitin (Ub1K48Ub2K48-Ub3K48Ub4):

The nucleophile in the form of $Ub1_{K48}Ub2_{K48}$ was ligated with electrophile $Ub3_{K48}Ub4$ for 30 hours to yield K48 linked tetra-ubiquitin with sulphur atoms attached to the ligation sites. The Ligation and transformation to tetra-ubiquitin was confirmed by mass spectrometry.

In particular, $Ub1_{K48}$-$Ub2_{K48}$, prepared according to step a (2.9 mg, 1.05 eq) and $Ub4$-$Ub3_{K48}$-SR prepared according to step b (2.8 mg, 1 eq), were dissolved in 162 µL of 6 M guanidine.HCl, 200 mM phosphate buffer pH ~7.0. To this solution 3.2 µL each of benzylmercaptan and thiophenol were added and incubated for 24 hours at 37° C. After 24 hours the reaction mixture was diluted with reaction buffer to 0.5 mM concentration and incubated for another 24 hours. The reaction was followed using an analytical column and a gradient of 5-15-40% B over 45 minutes. For preparative HPLC a similar gradient was used to afford the ligation product in 31% yield (~1.8 mg).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A process of chemically synthesizing a Poly-ubiquitin chain $Ub_n$, comprising n ubiquitin monomers linked by isopeptide bonds, n being an integer larger than 1, said process, which is devoid of any enzymatic synthesis of the Poly-ubiquitin chain $Ub_n$, comprising:

a) ligating a first Ubiquitin (Ub) thioester unit $Ub_m$-SR with a second Ubiquitin unit $Ub_q$, wherein:

said first Ubiquitin (Ub) thioester unit $Ub_m$-SR and said second Ubiquitin unit $Ub_q$ are prepared by chemical synthesis;

said Ub thioester unit $Ub_m$-SR contains m ubiquitin monomers, m being an integer ranging from 1 to (n−1);

at least one of said monomers is a chemically synthesized monomer containing p protected 1,2-thioamine-containing amino acids, p being an integer ranging from 1 to 7, R being selected from alkyl and aryl, and substituted or unsubstituted derivatives thereof;

said ubiquitin unit $Ub_q$ contains q ubiquitin monomers, q being an integer ranging from 1 to (n−1); and said $Ub_q$ contains at least one chemically synthesized monomer containing a non-protected 1,2-thioamine-containing amino acid, with the proviso that (m+q) is smaller or equal to n, to obtain a ligation product $Ub_{m+q}$ having (m+q) ubiquitin monomers and containing said p protected 1,2-thioamine-containing amino acids;

b) when (m+q)<n, de-masking at least one of said protected 1,2-thioamine-containing amino acids in said ligation product $Ub_{m+q}$ obtained in (a);

c) for (m+q)<n, repeating (a) and (b), x times, to obtain a ligation product $Ub_n$ having n Ub monomers in (x+1) steps, whereas in each step, $Ub_q$ is the ligation product $Ub_{m+q}$ obtained in the previous step, and $Ub_m$-SR is the same or different as the one used in the previous step; and d) desulfurization of said ligation product $Ub_n$ to obtain the Poly-ubiquitin chain $Ub_n$ having n ubiquitin monomers linked by isopeptide bonds.

2. The process of claim 1 wherein n ranges from 2 to 4.

3. The process of claim 1, wherein n is 2, x is 0, m is 1 and q is 1, to obtain a di-ubiquitin in one step.

4. The process of claim 1, wherein n is 3, x is 0, to obtain a tri-ubiquitin in one step, whereas:

i) m is 1 and q is 2; or
ii) m is 2 and q is 1.

5. The process of claim 1, wherein n is 3, x is 1, and m is 1 in each step, to obtain a tri-ubiquitin in two steps.

6. The process of claim 1, wherein n is 4 and x is 0 to obtain a tetra-ubiquitin in one step, whereas:

i) m is 2 and q is 2; or
ii) m is 1 and q is 3; or
iii) q is 1 and m is 3.

7. The process of claim 1, wherein n is 4, x is 2, and m is 1 in each step, to obtain a tetra-ubiquitin in two steps.

8. The process of claim 1, wherein said protected 1,2-thioamine containing amino acid is a protected mercaptolysine.

9. The process of claim 8, wherein said protected mercaptolysine is a thiazolidine (Thz)-protected mercaptolysine.

10. The process of claim 9, wherein said thiazolidine (Thz)-protected mercaptolysine has the general formula III:

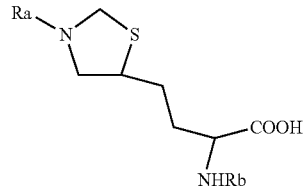

Formula III wherein Ra and Rb are independently either hydrogen or nitrogen protecting groups.

11. The process of claim 1, wherein p is 1 throughout said process.

12. The process of claim 1, wherein each of said p protected 1,2-thioamine-containing amino acids in said Ub thioester is located in one of the following positions of natural Lys in said Ub: one of the seven lysines in Ub K6, K11, K27, K29, K33, K48 and K63, replacing a lysine amino acid naturally located in said position.

13. The process of claim 1, to obtain a poly-ubiquitin chain Ubn containing at least one unnatural amino acid, whereas in one or more of said (x+1) steps of said process, at least one of said ubiquitin Ubq and/or said ubiquitin thioester Ubm-SR contain said at least one unnatural amino acid.

* * * * *